United States Patent [19]

McKendry

[11] Patent Number: 5,003,096
[45] Date of Patent: Mar. 26, 1991

[54] PREPARATION OF SUBSTITUTED 1,2,4-TRIAZOLO[1,4-A]PYRIMIDINE-2-SULFONANILIDES

[75] Inventor: Lennon H. McKendry, Midland, Mich.

[73] Assignee: The Dow Chemical Company, Midland, Mich.

[21] Appl. No.: 447,981

[22] Filed: Dec. 7, 1989

Related U.S. Application Data

[60] Division of Ser. No. 359,071, May 3, 1989, Pat. No. 4,910,306, which is a continuation of Ser. No. 118,495, Nov. 9, 1987, abandoned, which is a continuation-in-part of Ser. No. 795,818, Nov. 7, 1985, abandoned.

[51] Int. Cl.$^5$ .............................................. C07F 7/10
[52] U.S. Cl. .................................................... 556/410
[58] Field of Search .......................................... 556/410

[56] References Cited

U.S. PATENT DOCUMENTS

| | | | |
|---|---|---|---|
| 3,054,818 | 9/1962 | Pepe et al. | 556/410 |
| 3,328,450 | 6/1967 | Plueddermann | 556/410 X |
| 3,491,137 | 1/1970 | Zaweski et al. | 556/410 X |
| 3,927,057 | 12/1975 | Takamizawa et al. | 260/448.2 E |
| 4,189,249 | 2/1980 | Lambert | 556/410 X |
| 4,283,505 | 8/1981 | Kleeberg et al. | 556/410 X |
| 4,381,401 | 4/1983 | Poindexter | 556/410 |
| 4,416,876 | 11/1983 | Barcza et al. | 556/410 X |
| 4,490,306 | 12/1984 | Acker | 260/465 E |
| 4,623,739 | 11/1986 | Watanabe | 556/410 |
| 4,741,764 | 5/1988 | Kieschick et al. | 71/92 |
| 4,910,306 | 3/1990 | McKendry | 556/410 X |

FOREIGN PATENT DOCUMENTS

| | | | |
|---|---|---|---|
| 2002066 | 7/1971 | Fed. Rep. of Germany | 556/410 X |
| 951652 | 3/1964 | United Kingdom | 556/410 X |
| 1334393 | 10/1973 | United Kingdom | 556/410 X |

OTHER PUBLICATIONS

Porskamp et al., *Synthesis*, 368–369 (1981).
Anderson, *J. Am. Chem. Soc.*, 73, 5802 (1951).
Bowser et al., *J. Org. Chem.*, 48, 4111–13 (1983).
Birkofer et al., *Chem. Ber.*, 93, 2810–13 (1960).
Oliver and Graham, *J. Organometal Chem.*, 19, 17–27 (1969).
Scherer, *Organometallic Chemistry Reviews*, 3A, 281–309 (1968).
Ando and Tsumaki, *Synthesis*, 263–4 (1982).
Cullis et al., *Chem. Abs.*, 102, 116206a (1985).
Maringgele and Meller, *Chem. Abs.* 91, 74669A (1979).
Maringgele and Meller, *Chem. Abs.*, 90, 121702x (1979).

*Primary Examiner*—Paul F. Shaver
*Attorney, Agent, or Firm*—D. Wendell Osborne

[57] ABSTRACT

Substituted 1,2,4-triazolo[1,5-a]pyrimidine-2-sulfonanilides, which are known herbicides, are prepared by the reaction of substituted 1,2,4-triazolo[1,5-a]-pyrimidine-2-sulfonyl halides with substituted N-trialkylsilylanilines in the presence of a base catalyst. The method is especially useful for the preparation of substituted 1,2,4-triazolo[1,5-a]pyrimidine-2-sulfonanilides derived from substituted anilines having both 2- and 6-substituents, at least one of which is electron withdrawing, such as N-(2,6-dichlorophenyl)-5,7-dimethyl-1,2,4-triazolo[1,5-a]pyrimidine-2-sulfonamide. N-trialkylsilylanilines having both 2- and 6-substituents, at least one of which is electron withdrawing, such as N-trimethylsilyl-2,6-dichloro-3-methylaniline, are described.

6 Claims, No Drawings

PREPARATION OF SUBSTITUTED 1,2,4-TRIAZOLO[1,4-A]PYRIMIDINE-2-SULFONANILIDES

CROSS-REFERENCE TO RELATED APPLICATION

This is a divisional of application Ser. No. 359,071, filed May 30, 1989, now U.S. Pat. No. 4,910,306, which is a continuation of application Ser. No. 118,495, filed Nov. 9, 1987, now abandoned, which is a continuation-in-part of application Ser. No. 795,818, filed Nov. 7, 1985 now abandoned.

BACKGROUND OF THE INVENTION

Substituted 1,2,4-triazolo[1,5-a]pyrimidine-2-sulfonanilides such as those described in EP Application No. 142152A published May 22, 1985 are valuable herbicides for the selective control of weeds in agronomic crops. A known method for the preparation of substituted 1,2,4-triazolo[1,5-a]pyrimidine-2-sulfonanilides involves the reaction of substituted 1,2,4-triazolo[1,5-a]pyrimidine-2-sulfonyl halides with either a substituted aniline in the presence of a tertiary amine base (EP Application No. 142152A) or an excess of aniline (British Patent No. 951,652). This type of procedure is generally satisfactory for the preparation of substituted 1,2,4-triazolo[1,5-a]pyrimidine-2-sulfonanilides wherein the substituted aniline employed is aniline itself or is a substituted derivative of aniline that has similar reactivity as a nucleophilic reagent. When the substituted aniline reactant is of substantially reduced nucleophilic reactivity due to the presence of electron withdrawing substituents on the ring and, especially, to the presence of such substituents in the positions ortho to the amino function, this method is very slow and provides low yields of the desired products. This reactivity problem is particularly unfortunate because the most herbicidally potent substituted 1,2,4-triazolo[1,5-a]pyrimidine-2-sulfonanilides possess such substituents.

In order to circumvent the reactivity problem, Kleschick et al. (EP Application No. 142152A) employed a strong base, such as an alkali metal alkyl or an alkali metal hydride, capable of converting the poorly nucleophilic substituted aniline to its corresponding metal derivative in place of the tertiary amine base. The metal derivative was preformed and then allowed to react with a substituted 1,2,4-triazolo[1,5-a]pyrimidine-2-sulfonyl halide. This procedure allows the compounds to be prepared, but it requires an excess of the metal derivative of the substituted aniline and is carried out below 0° C., and, therefore, is not commercially desirable. In view of the herbicidal properties of substituted 1,2,4-triazolo[1,5-a]pyrimidine-2-sulfonanilides, it is desirable to have improved processes for their preparation that produce them in high yields and in a relatively short reaction period.

SUMMARY OF THE INVENTION

This invention relates to a novel process of preparing substituted 1,2,4-triazolo[1,5-a]pyrimidine-2-sulfonanilides, including those derived from substituted anilines having reduced nucleophilic reactivity, readily and in good yield, and to certain of the starting materials employed.

It has now been found that substituted 1,2,4-triazolo[1,5-a]pyrimidine-2-sulfonanilides of Formula I can be prepared readily and in good yield by the reaction of a substituted 1,2,4-triazolo[1,5-a]pyrimidine-2-sulfonyl halide of Formula II, with a substituted N-trialkylsilylaniline of Formula III, the reaction being preferably carried out in the presence of a tertiary amine or dimethyl sulfoxide base catalyst. The reaction mixture obtained is thereafter treated with an aqueous reagent. The process can be represented as follows:

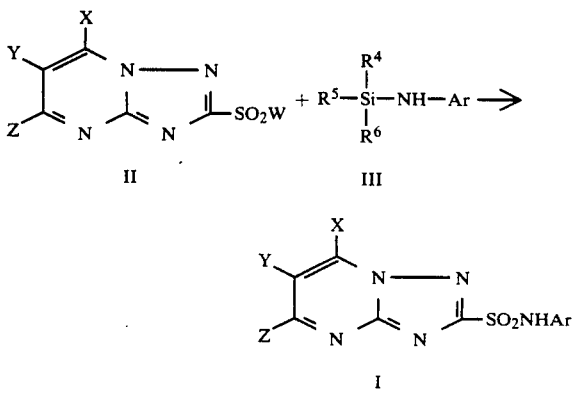

In the foregoing

X, Y and Z independently represent H, F, Cl, Br, I, R, OR, SR, or $CF_3$;

R, $R^4$, $R^5$, and $R^6$ independently represent $C_1$–$C_4$ alkyl,

W represents Cl or Br,

Ar represents phenyl having up to 4 substituents selected from the group consisting of F, Cl, Br, I, $NO_2$, $CF_3$, R, OR, SR, SOR, $SO_2R$, and $CO_2R^7$; and $R^7$ represents $C_1$–$C_4$ alkyl, $C_2$–$C_4$ alkenyl, $C_2$–$C_4$ alkynyl, or 2-ethoxyethyl.

The method of this invention is especially useful for the preparation of compounds of Formula I in which Ar is substituted in the 2 and 6 positions, at least one substituent of which is electron withdrawing, and, optionally, is substituted at the 3-position. In this preferred embodiment Ar represents

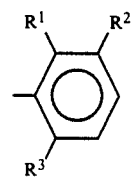

wherein $R^1$ represents F, Cl, Br, I, $NO_2$, $CF_3$, R, SR or $CO_2R^7$;

$R^2$ represents H, F, Cl, Br, I, R or $CO_2R^7$;

$R^3$ represents F, Cl, Br, I, $NO_2$, R, OR, $CO_2R^7$ or phenyl;

X, Y, and Z, independently represent H, F, Cl, Br, I, R, OR, SR, or $CF_3$;

R represents $C_1$–$C_4$ alkyl; and $R^7$ represents $C_1$–$C_4$ alkyl, $C_2$–$C_4$ alkenyl, $C_2$–$C_4$ alkynyl, or 2-ethoxyethyl;

with the proviso that $R^1$ and $R^2$ cannot both be R.

These compounds are particularly potent 1,2,4-triazolo[1,5-a]pyrimidine-2-sulfonanilide herbicides.

The starting material substituted N-trialkylsilylanilines, III, required for the preferred embodiment of this invention are novel compounds.

DETAILED DESCRIPTION OF THE INVENTION

The reaction of the present invention generally proceeds readily and provides good yields of the desired 1,2,4-triazolo[1,5-a]pyrimidine-2-sulfonanilides (I), irrespective of the substituents present on either of the reactants; N-trialkylsilylanilines (III) and 1,2,4-triazolo[1,5-a]pyrimidine-2-sulfonyl halides (II). The ease with which the reaction takes place, however, varies depending on the substituents present and the reaction conditions for obtaining optimum yields and desired reaction rates vary accordingly.

The process is conducted by first combining compounds of Formula II with compounds of Formula III and a tertiary amine or dimethyl sulfoxide base catalyst and allowing them to react. The reactants can be combined in any order, but it is often convenient to first combine the base catalyst with the 1,2,4-triazolo[1,5-a]pyrimidine-2-sulfonyl halide and subsequently add the N-trialkylsilylaniline or to combine the 1,2,4-triazolo[1,5-a]pyrimidine-2-sulfonyl halide and N-trialkylsilylaniline and subsequently add the base catalyst. The exact relative proportions of II, III, and base catalyst employed are not critical, but for the best results about 1 to about 3 moles of III and about 0.05 to about 2 moles of catalyst are employed for each mole of II present. When the catalyst is dimethyl sulfoxide less than 0.5 moles is typical, but when it is a tertiary amine more than 1 mole is employed.

The base catalyst for the process can be a tertiary amine, such as triethylamine, trimethylamine, N,N-diethylbenzylamine, N,N-dimethylaniline, pyridine, 4-dimethylaminopyridine, 4-picoline, or 2,4-lutidine, or dimethyl sulfoxide. Pyridine and dimethyl sulfoxide are preferred base catalysts.

An inert organic solvent is generally employed in the process. Useful solvents include toluene, hexane, tetrahydrofuran, dioxane, acetonitrile, ethyl acetate, methyl ethyl ketone, methylene chloride, and the like. Acetonitrile is preferred.

It is further preferred to conduct this step of the process under substantially anhydrous conditions. This can be achieved by using dry reagents and solvents and conducting the reaction in a closed system or under an inert gas blanket. It is further preferred to agitate the reaction mixture.

The above reaction can be conducted at temperatures from about 5° C. to about 115° C., and preferably in the range of about 20° C. to about 90° C. The reaction is generally continued until the starting material of Formula II is consumed, which requires a few minutes to about 24 hours depending on the starting materials employed, the catalyst identity and concentration, the solvent employed, and the temperature. Suitable conditions within those described can readily be chosen by one skilled in the art by analytically monitoring the disappearance of the reactant of Formula II and adjusting the reaction conditions appropriately to utilize the process for any combination of the starting materials.

The reaction mixture obtained in the above described operations is next preferably treated with an aqueous reagent to hydrolyze any N-trialkylsilyl-1,2,4-triazolo[1,5-a]pyrimidine-2-sulfonanilide present. Hydrolysis occurs readily with all aqueous reagents including water, dilute aqueous acids, dilute aqueous bases and other solutions containing water and special reaction conditions are not required. Typical aqueous reagents include 1N hydrochloric acid and 0.5N sodium hydroxide.

The reaction products of Formula I prepared by the process can be isolated by conventional methods, such as evaporation of volatile components, extraction, crystallization, and chromatography. Typically, the solvent is removed by evaporation; the product is dissolved in aqueous alkali and extracted with an organic solvent to remove non-polar impurities; and then the product is precipitated by the addition of aqueous acid and, if required, further purified by recrystallization or liquid chromatography.

The substituted 1,2,4-triazolo[1,5-a]pyrimidine-2-sulfonyl halide starting materials (II) utilized in the process of this invention are prepared as described in EP Application No. 142152A or by other conventional methods. Examples of suitable reactants of Formula II include the following: 5,7-dimethyl-1,2,4-triazolo[1,5-a]pyrimidine-2-sulfonyl chloride, 5-methyl-1,2,4-triazolo[1,5-a]pyrimidine-2-sulfonyl chloride, 5-methyl-7-trifluoromethyl-1,2,4-triazolo[1,5-a]pyrimidine-2-sulfonyl bromide, 1,2,4-triazolo[1,5-a]pyrimidine-2-sulfonyl chloride, 5-methoxy-7-butyl-1,2,4-triazolo[1,5-a]pyrimidine-2-sulfonyl bromide, 6-chloro-1,2,4-triazolo[1,5-a]pyrimidine-2-sulfonyl chloride, 5-methylethyl-7-methylthio-1,2,4-triazolo[1,5-a]pyrimidine-2-sulfonyl chloride, 5,7-dimethyl-6-fluoro-1,2,4-triazolo[1,5-a]pyrimidine-2-sulfonyl chloride and 5,7-dimethoxy-1,2,4-triazolo[1,5-a]pyrimidine-2-sulfonyl chloride.

Substituted N-trialkylsilylaniline compounds (III) are a little known class of compounds. Only a few examples have been reported in the literature (e.g., Synthesis 368(1981), J. Organometal Chem 19, 17(1969) and U.S. Pat. No. 4,490,306). In particular, compounds of Formula III having substituents in both the 2 and 6 positions, at least one of which is electron withdrawing, are novel. These particular substituted N-trialkylsilylanilines, which are especially useful in the present process because the compounds of Formula I produced from them constitute an especially potent group of substituted 1,2,4-triazolo[1,5-a]pyrimidine-2-sulfonanilide herbicides, are defined by the formula:

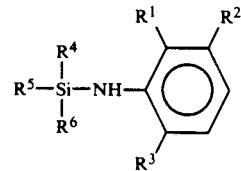

wherein
$R^1$ represents F, Cl, Br, I, $NO_2$, $CF_3$, R, SR or $CO_2R^7$;
$R^2$ represents H, F, Cl, Br, I, R or $CO_2R^7$;
$R^3$ represents F, Cl, Br, I, $NO_2$, R, OR, $CO_2R^7$, or phenyl;
R represents $C_1$-$C_4$ alkyl;
$R^4$, $R^5$, and $R^6$ independently represent $C_1$-$C_4$ alkyl; and
$R^7$ represents $C_1$-$C_4$ alkyl, $C_2$-$C_4$ alkenyl, $C_2$-$C_4$ alkynyl, or 2-ethoxyethyl;
with the proviso that $R^1$ and $R^3$ cannot both be alkyl.

Representative substituted N-trialkylsilylanilines of the above type include N-trimethylsilyl-2,6- dichloroaniline, methyl N-trimethylsilyl-3-fluoroanthranilate, N-trimethylsilyl-2,6-dichloro-3-methylaniline, N-trimethylsilyl-2,6-difluoroaniline, N-triethylsilyl-2-methoxy-6-trifluoromethylaniline, N-triethylsilyl-2,6-difluoro-3-methylaniline, N-butyldimethylsilyl-2-bromo-6-phenylaniline, N-triethylsilyl-2-chloro-6-(methylthio)aniline, N-tripropylsilyl-2-butyl-6-nitroaniline, N-triethylsilyl-2,3-dimethyl-6-iodoaniline, and allyl N-triethylsilyl-3-chloroanthranilate.

Substituted N-trialkylsilylanilines (III) can be prepared by the reaction of a trialkylsilyl halide with an excess of an appropriate substituted aniline or with an approximately equal molar quantity of an appropriate substituted aniline in combination with a tertiary amine base. (See, for example, U.S. Pat. No. 3,927,057 and Synthesis 368(1981)). Typically, the substituted aniline, excess tertiary amine, and trialkylsilyl halide are combined in an inert organic solvent and agitated at between room temperature and 115° C. After completion of the reaction, the mixture is filtered or extracted with water to remove the tertiary amine hydrohalide by-product and distilled to isolate the product. A trialkylsilyl bromide or chloride is commonly employed as the trialkylsilyl halide. Typical tertiary amines include triethylamine and pyridine and typical solvents employed are benzene, toluene and carbon tetrachloride.

Many of the substituted anilines required for the preparation of the N-trialkylsilylanilines of this invention are available commercially. The preparation of those not commercially available, in particular those having both 2- and 6-substituents, one of which is electron withdrawing, is given in EP Application No. 142152A.

The following examples are illustrative of the invention and should not be construed as limiting the scope.

EXAMPLE 1

Preparation of

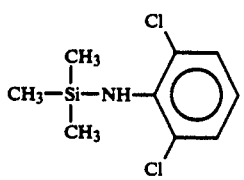

A solution of 60 ml of benzene, 5.0 g (30.9 mmole) of 2,6-dichloroaniline, 10.6 ml (76.0 mmole) of triethylamine, and 8.08 ml (61.1 mmole) of trimethylsilyl bromide was heated at reflux for 54 hours, cooled, filtered, and the solvent was removed from the filtrate in vacuo. The residue was evacuated at 1 mm to remove any excess trimethylsilyl bromide. The residual mixture was filtered into a round-bottomed flask and distilled using a short Vigreaux column to provide 5.43 g (23.2 mmole, 75.0 percent yield) of the N-trimethylsilyl-2,6-dichloroaniline as a 97 percent pure amber oil, bp 74° C.-75° C. at 0.4 mm.

NMR (CCl$_4$+TMS): δ7.21 (two doublets, 7.0 Hz, 9.0 Hz, Ph-H$_3$ and Ph-H$_5$), δ6.62 (d of d, 7.0 Hz, 9.0 Hz, Ph-H$_4$), δ4.0 (broad s, NH), δ0.31 (s, Si(CH$_3$)$_3$).

IR (film): 3400 cm$^{-1}$ (NH), 2980 cm$^{-1}$ (CH$_3$), 1585$^{-1}$ (Ar-N).

EXAMPLE 2

Preparation of

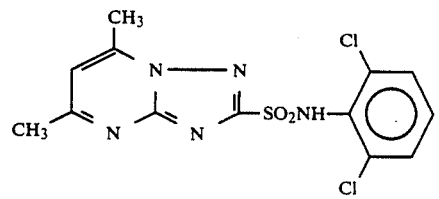

A solution consisting of 102.4 mg (0.415 mmole) of 2-chlorosulfonyl-5,7-dimethyl-1,2,4-triazolo[1,5-a]pyrimidine, 2.0 ml of acetonitrile, and 33.6 μl (0.415 mmole) of pyridine was stirred 5 minutes. N-trimethylsilyl-2,6-dichloroaniline, 86.9 μl (0.456 mmole) was added. The solution was stirred at room temperature for 16 hours and the reaction monitored by thin layer chromatography and by reverse phase HPLC. The 2-chlorosulfonyl compound gradually disappeared and a new peak appeared. The reaction was about 10-30 percent complete after 16 hours. An additional 33.6 μl of pyridine was added and the solution heated at 65° C. for 4 hours and at reflux for 16 hours. The solvent was removed under nitrogen and the residue treated with 4 ml of 0.5N NaOH and stirred for 0.5 hour. The solution was extracted with CH$_2$Cl$_2$, acidified with concentrated HCl and filtered. The precipitate was washed with water and dissolved in CH$_3$CN. The resulting solution was heated to reflux, filtered through silica gel and the solvent removed in vacuo to obtain 119 mg (0.321 mmole, 77.2 percent yield) of N-(2,6-dichlorophenyl)-5,7-dimethyl-1,2,4-triazolo[1,5-a]pyrimidine-2-sulfonamide as a light yellow solid. The product was further purified by washing with acetone, and recrystallizing from refluxing CH$_3$CN to obtain 91.5 mg (0.246 mmole) of product as a white powder, m.p. 263°-265° C.

| Analysis | C | H | N |
| --- | --- | --- | --- |
| Calcd. for C$_{13}$H$_{11}$C$_{12}$N$_5$O$_2$S | 41.95 | 2.98 | 18.81 |
| Found | 41.80 | 3.04 | 18.85 |

EXAMPLE 3

Preparation of

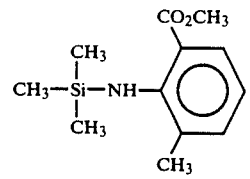

A solution of 10 ml of benzene, 1.0 g (6.05 mmole) of methyl 3-methylanthranilate, 1.46 ml (11.1 mmole) of trimethylsilyl bromide, and 1.54 ml (11.0 mmole) of triethylamine was stirred at room temperature for 20 hours and at 45° C. for 2 hours.

The product was isolated and purified as described in Example 1 to provide 95 percent pure methyl N-trimethylsilyl-3-methylanthranilate, b.p. 64° C. at 0.05 mm.

NMR (CCl$_4$+TMS): δ7.66 (d of d, 7.5 Hz, 1.5 Hz, Ph-H$_6$), δ7.3 (broad s, NH), δ7.09 (broad d, 7.5 Hz, Ph-H$_4$), δ6.53 (t, 7.5 Hz, Ph-H$_5$) δ3.80 (s, OCH$_3$) δ2.29 (s, PhCH$_3$), δ0.2 (s, Si(CH$_3$)$_3$).

EXAMPLE 4

Preparation of

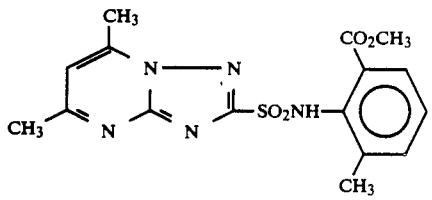

A solution consisting of 145.9 mg (0.615 mmole) of methyl N-trimethylsilyl-3-methylanthranilate, 1 ml of CH$_3$CN, and 80.4 mg (0.326 mmole) of 2-chlorosulfonyl-5,7-dimethyl-1,2,4-triazolo[1,5-a]pyrimidine was stirred at room temperature and the reaction monitored by reverse phase HPLC. The reaction was about 30 percent complete after 4 hours. Pyridine, 29.1 μl (0.360 mmole), was added and the solution stirred for 10 min and again analyzed. Complete reaction had occurred. The solution was allowed to stand overnight. The CH$_3$CN was removed under a nitrogen atmosphere and the residue treated with 2 ml of 1.0N HCl and 2 ml of CH$_2$Cl$_2$. The CH$_2$Cl$_2$ phase was transferred to a column containing 50 g of silica gel and chromatographed to obtain 112.5 mg of N-(2-methoxycarbonyl-6-methylphenyl)-5,7-dimethyl-1,2,4-triazolo[1,5-a]pyrimidine-2-sulfonamide (0.300 mmole, 92.0 percent yield) as a white crystalline solid, m.p. 181°–182° C. The solid was dissolved in CHCl$_3$ and the solvent again removed in vacuo affording the product as a light yellow powder, m.p. 192°–194° C.

| Analysis | C | H | N |
| --- | --- | --- | --- |
| Calcd. for C$_{16}$H$_{17}$N$_5$O$_4$S | 51.19 | 4.56 | 18.66 |
| Found | 51.20 | 4.64 | 18.69 |

EXAMPLE 5

Preparation of

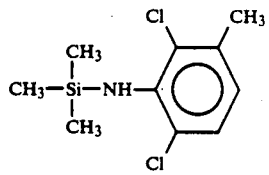

A solution of 50 ml of benzene, 4.0 g (22.7 mmole) of 2,6-dichloro-3-methylaniline, 10.67 ml (80.8 mmole) of trimethylsilyl bromide, and 13.1 ml (94.0 mmole) of triethylamine was heated at reflux over 42 hours. The product was isolated as described in Example 1 to provide 4.14 g (16.7 mmole, 73.5 percent yield) of 98.0 percent pure N-trimethylsilyl-2,6-dichloro-3-methylaniline as a light yellow oil, b.p. 64°–68° C. at 0.03 mm.

NMR (CCl$_4$+TMS): δ6.97 (d, 8.0 Hz, Ph-H$_5$), δ6.49 (d, 8.0 Hz, Ph-H$_4$), δ3.94 (broad s, NH), δ2.28 (s, Ph-CH$_3$), δ0.29 (s, Si(CH$_3$)$_3$).

EXAMPLE 6

Preparation

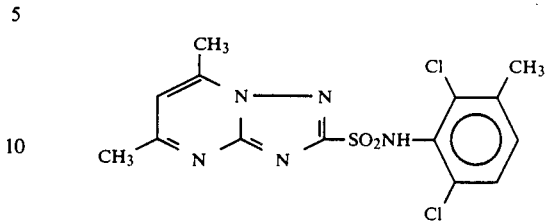

A solution consisting of 106.8 mg (0.433 mmole) of 2-chlorosulfonyl-5,7-dimethyl-1,2,4-triazolo[1,5-a]pyrimidine, 0.5 ml of CH$_3$CN, and 252 μl (1.30 mmole) of N-trimethylsilyl-3-methyl-2,6-dichloroaniline was stirred at room temperature and 10 μl (0.14 mmole) of dimethyl sulfoxide (DMSO) added dropwise. The solution was stirred for 2 hours during which time a precipitate formed. The CH$_3$CN was removed under nitrogen and the residual solid treated with 1 ml of 1N HCl. The mixture was stirred for 10 min, filtered, and the precipitate washed with acetone to obtain 136 mg of N-(2,6-dichloro-3-methylphenyl)-5,7-dimethyl-1,2,4-triazolo[1,5-a]pyrimidine-2-sulfonamide product as an off-white solid. The solid was washed with methanol and dried to give 120 mg (0.310 mmole, 71.6 percent yield) of product as a white solid, m.p. 286.5°–288° C.

| Analysis | C | H | N |
| --- | --- | --- | --- |
| Calcd. for C$_{14}$H$_{13}$Cl$_2$N$_5$O$_2$S | 43.54 | 3.39 | 18.13 |
| Found | 43.50 | 3.54 | 18.13 |

EXAMPLE 7

Preparation of

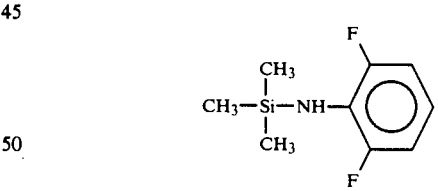

Trimethylsilyl bromide, 10.24 ml (77.5 mmole), was added to 6 ml (55.7 mmole) of 2,6-difluoroaniline in 70 ml of benzene. There was a slight exotherm and immediate precipitation. Triethylamine, 10.8 ml (77.5 mmole), was added and the mixture stirred at room temperature for 16 hours. The mixture was filtered and the solvent removed from the filtrate in vacuo. The product was purified as described in Example 1 to provide 8.85 g (51.1 mmole, 91.7 percent yield) of 99.3 percent pure N-trimethylsilyl-2,6-difluoroaniline as a colorless liquid, b.p. 89°–91° C. at 18 mm.

NMR (CCl$_4$+TMS): δ6.5 (complex, 3H, Ar-H), δ3.35 (broad s, 1H, NH) δ0.19 (t, 0.5 Hz, 9H, Si(CH$_3$)$_3$).

EXAMPLE 8

Preparation of

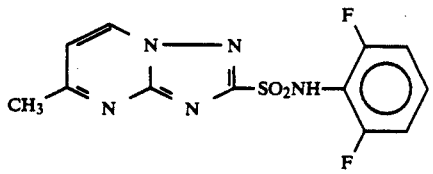

A solution consisting of 91.4 mg of about 77 percent pure 2-chlorosulfonyl-5-methyl-1,2,4-triazolo-[1,5-a]pyrimidine (0.30 mmole), 0.5 ml of CH$_3$CN, 0.5 ml of N-trimethylsilyl-2,6-difluoroaniline, and 10 μl (0.141 mmole) of dimethyl sulfoxide was stirred at room temperature for 4 hours. The solution was treated with 2 ml of 1.0N HCl and the resultant mixture filtered. The precipitate was dried in vacuo, washed with CH$_2$Cl$_2$ and again dried to afford 68.7 mg (0.211 mmole, 70.0 percent yield) of N-(2,6-difluorophenyl)-5-methyl-1,2,4-triazolo[1,5-a]pyrimidine-2-sulfonamide product as a white powder, m.p. 250°–251° C.

| Analysis | C | H | N |
|---|---|---|---|
| Calcd. for C$_{12}$H$_9$F$_2$N$_5$O$_2$S | 44.31 | 2.79 | 21.53 |
| Found | 44.10 | 3.03 | 21.00 |

What is claimed is:

1. A compound of the formula

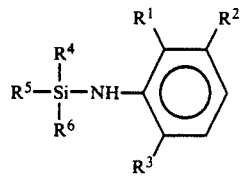

wherein
  $R^1$ represents F, Cl, Br, I, NO$_2$, CF$_3$, R, SR or CO$_2$R$^7$;
  $R^2$ represents H, F, Cl, Br, I, R or CO$_2$R$^7$;
  $R^3$ represents F, Cl, Br, I, NO$_2$, R, OR, CO$_2$R$^7$ or phenyl;
  $R^4$, $R^5$ and $R^6$ independently represent C$_1$–C$_4$ alkyl;
  R represents C$_1$–C$_4$ alkyl; and
  $R^7$ represents C$_1$–C$_4$ alkyl, C$_2$–C$_4$ alkenyl, C$_2$–C$_4$ alkynyl, or 2-ethoxyethyl;
  with the proviso that $R^1$ and $R^3$ do not both represent R.

2. A compound of claim 1 wherein $R^4$, $R^5$, and $R^6$ each represent methyl.

3. The compound of claim 2: N-trimethylsilyl-2,6-dichloroaniline.

4. The compound of claim 2: methyl N-trimethylsilyl-3-methylanthranilate.

5. The compound of claim 2: N-trimethylsilyl-2,6-dichloro-3-methylaniline.

6. The compound of claim 2: N-trimethylsilyl-2,6-difluoroaniline.

* * * * *